United States Patent [19]

Wronka

[11] 4,041,102

[45] Aug. 9, 1977

[54] CAUSTIC TREATMENT OF ALKYLATE-CONTAINING HYDROCARBON

[75] Inventor: John A. Wronka, Pennsauken, N.J.

[73] Assignee: Cities Service Company, Tulsa, Okla.

[21] Appl. No.: 613,007

[22] Filed: Sept. 12, 1975

[51] Int. Cl.$^2$ .............................................. C07C 3/54
[52] U.S. Cl. .......................... 260/683.62; 260/683.63
[58] Field of Search ..................... 260/683.59, 683.62, 260/683.63

[56] References Cited

U.S. PATENT DOCUMENTS

| | | | |
|---|---|---|---|
| 2,425,572 | 8/1947 | Slotterbeck | 260/683.63 |
| 3,013,093 | 12/1961 | Stiles | 260/683.62 |
| 3,239,578 | 3/1966 | Samuelson | 260/683.62 |
| 3,551,514 | 12/1970 | Evering | 260/683.63 |
| 3,655,807 | 4/1972 | Rakow et al. | 260/683.63 |

*Primary Examiner*—George Crasanakis
*Attorney, Agent, or Firm*—George L. Rushton; John W. Carpenter

[57] ABSTRACT

An improved process for treating a hydrocarbon stream exiting the hydrocarbon-acid separator of an anionic surfactant promoted, sulfuric acid catalyzed, light olefinisoparaffin alkylation unit wherein the stream contains the alkylate, excess isoparaffins, traces of the acid alkylation catalyst, and an anionic surface-active alkylation promoter. The improvement comprises mixing, prior to introducing into a hydrocarbon-caustic separator, the hydrocarbon stream with a water-caustic solution having at least 15% by wt. concentration of caustic such that the salt of the promoter appears as a flocculent precipitate at the hydrocarbon-water-caustic solution interface in the hydrocarbon-caustic separator.

3 Claims, No Drawings

CAUSTIC TREATMENT OF ALKYLATE-CONTAINING HYDROCARBON

BACKGROUND OF THE INVENTION

1. Field of the Invention

The present invention relates to a downstream processing of alkylate from low molecular weight olefin-isoparaffin polymerization using a sulfuric acid catalyst promoted with an anionic type surface agent. More particularly, the present invention provides an improvement in downstream processing of gasoline production from alkylation using sulfuric acid.

2. Description of the Prior Art

Alkylation, in its broadest meaning, can be described as the addition or insertion of an alkyl group into a molecule. These alkylation reactions are diverse in nature and there is no inclusive or universal method of conducting alkylations. Each alkylation reaction is subject to its particular requirements as to free energy change, equilibrium, heat of reaction, equipment, catalyst, etc.

In the petroleum industry, the term alkylation is used in a more restricted sense to describe the addition of a low molecular weight hydrocarbon containing a tertiary hydrogen to an olefin to produce highly branched chain paraffins mainly in the $C_7$-$C_9$ range which are high quality fuels for ignition engines. In commercial processes of this type, concentrated sulfuric acid and hydrofluoric acid are used.

In the case of these sulfuric acid alkylation processes, it has been shown that the addition of certain materials can result in improvements to the process. As examples: U.S. Pat. No. 2,276,251 teaches the use of organic bases such as amides, amines, imides, imines, pyridines, picolines, lutidenes, and collidenes; U.S. Pat. No. 2,375,637 teaches sulfur, selenium, tellurim, salts of condensation products of halogenated chlorosulfonic acids with amides of fatty acids, salts of amides, substituted amides of fatty acids, and salts of the sulfuric acid ester of aliphatic alcohols; U.S. Pat. No. 3,364,280 teaches surface active sulfonium or phosphonium salts; U.S. Pat. No. 3,231,633 teaches large, stable, surface-active cations; U.S. Pat. No. 3,551,514 discloses sodium stearate; U.S. Pat. No. 3,655,807 discloses dodecylbenzene sulfonic acid; U.S. Pat. No. 3,689,590 teaches p-Phenylenediamine; and U.S. Pat. No. 3,231,633 teaches triphenylmethylchloride, tetramethyl ammonium chloride, and trimethyl phosphonium chloride.

Many of the above suggested alkylation promoters are surface-active agents. For convenience, surface-active agents are classified as being anionic, cationic, nonionic or amphoteric depending upon the actual or potential charge on the surface-active portion of the molecule. It is the chemical nature of anionic surface-active agents such as dodecylbenzene sulfonic acid, stearic acid, and sulfuric acid esters of aliphatic alcohols to partition between the acid and hydrocarbon phases in a sulfuric acid catalyzed alkylation process. As a consequence, the alkylate produced in processes using these promoters can be expected to contain some of the surface-active material in the alkylate itself.

An essential feature of practical sulfuric acid catalyzed alkylation processes is that the alkylate as produced should not contain trace quantities of sulfuric acid which can lead to severe corrosion problems downstream. In practice, alkylate is separated in a sulfuric acid catalyzed system by gravity. Under conditions normally employed, trace quantities of sulfuric acid remain in the alkylate. In order to elminate the downstream corrosion problems referred to, it is customary to neutralize or remove the acid by passing the alkylate through successive caustic scrub and water-wash steps. When using anionic-type surface-active promoters, the presence of these surface-active materials in the alkylate cause severe emulsification and interface problems so as to limit their practical utility. It is the purpose of this invention to describe a process in which these downstream operational problems are eliminated or minimized for alkylates containing trace quantities of anionic surface-active materials such as that produced by an anionic surface-active agent promoted sulfuric acid catalyzed alkylation process.

SUMMARY OF THE INVENTION

It is therefore an object of the present invention to provide an improvement in the downstream processing of alkylate from an anionic-type surface-active agent promoted sulfuric acid catalyzed alkylation It is another object of the present invention to provide an improvement in the downstream processing of alkylate from anionic-type surface-active agent promoted sulfuric acid catalyzed alkylation such that the salt of the surface active alkylation promoter appears as a flocculent precipitate at the hydrocarbon-water-caustic solution interface in the hydrocarbon caustic separator.

The foregoing objects are achieved by the practice of this invention. Broadly, the invention is an improved continuous process for the downstream processing of alkylate which exits as a hydrocarbon stream from the hydrocarbon-acid separator of an alkylation unit wherein the stream contains the alkylate, excess isoparaffins, and traces of the sulfuric acid alkylation catalyst and surface active alkylation promoter. The improvement comprises mixing, prior to introducing into a hydrocarbon-caustic separator, the hydrocarbon stream with a water-caustic solution having at least 15% by wt. concentration of caustic such that the salt of the promoter appears as a flocculent precipitate at the hydrocarbon-water-caustic solution interface in the hydrocarbon-caustic separator.

DETAILED DECRIPTION OF THE INVENTION

The process of the present invention is an improvement upon the downstream processing of a low molecular weight olefin-isoparaffin alkylate exiting the hydrocarbon-acid separator of an anionic surface active agent promoted sulfuric acid catalyzed continuous alkylation unit.

Alkylation, in its broadest meaning, can be described as the addition or insertion of an alkyl group into a molecule. These alkylation reactions are diverse in nature and there is no inclusive or universal method of conducting alkylations. Each alkylation is subject to its particular requirements as to free energy change, equilibrium, heat of reaction, equipment, catalyst, etc.

In the petroleum industry, the term alkylation is used in a more restricted sense to describe the addition of a low molecular weight hydrocarbon containing a tertiary hydrogen to an olefin to produce highly branched chain paraffins in the $C_7$-$C_9$ range which are high quality fuels for ignition engines. In these processes, the isoparaffins are contacted with olefins in the presence of a suitable catalyst to produce the desired branched chain paraffinic isomers.

Catalysts used in the above-type alkylation processes include sulfuric acid, hydrofluoric acid, boron trifluoride, aluminum chloride, and double halides of alkali metals with aluminum and hydrogen fluoride. Acid catalysts such as sulfuric or hydrofluoric acid are most common. Sulfuric acid has been sidely used as the catalyst in most commercial installations.

In the utilization of the sulfuric acid process, normally the low molecular weight isoparaffins and olefins are reacted at pressures up to about 500 psi and temperatures ranging from about 100° F down to below 0° F. Isobutane and $C_2$-$C_6$ olefins are the more commonly used feed materials.

It has been further shown that a promoter can be introduced into the alkylation process for the improvement of quality and yield of the alkylates produced. Some promoters which have been suggested for use in this manner are: organic bases, such as amides, imides, imines, pyridines, picolines, lutidines and collidines; sulfur; selenium; tellurium; salts of condensation products of halogenated chlorosulfonic acids with amides of fatty acids; salts of amides; substituted amides of fatty acids; salts of the sulfuric acid ester of aliphatic alcohols; surface active sulfonium or phosphonium salts; large, stable, surface-active cations; sodium stearate; dodecylbenzenesulfonic acid; p-phenylenediamine; triphenylmethylchloride; tetramethylammonium chloride; and trimethylphosphonium chloride.

Many of the above listed promoters are surface-active agents. For convenience, surface-active agents are classified as being anionic, cationic, non-ionic, or amphoteric depending upon the actual or potential charge on the surface-active portion of the molecule. Of special interest in this invention are surface-active type promoters of the anionic type such as dodecylbenzene sulfonic acid, stearic acid, dihexylsulfophthalate, and similar compounds. It is the chemical nature of these anionic-type surface active agents to partition between the acid and hydrocarbon phases in an anionic surface active agent promoted sulfuric acid catalyzed alkylation process so that alkylate exiting the reactor will contain some surface active agent.

In a typical sulfuric acid alkylation process for the production of motor fuel; following the alkylation step, the acid catalyst is permitted to separate from the hydrocarbon-acid emulsion stream by gravity. The resulting hydrocarbon stream includes alkylate, excess isoparaffins, traces of acid alkylation catalyst, and some anionic-type surface active agent when promoted with such a material. The hydrocarbon stream is subsequently subjected to various vaporization and distillation fractionations to separate unreacted components and various products. Since in a preferred embodiment the feed materials are isobutane and butene, the alkylate is predominantly 2,2,3 trimethylpentane.

The presence of trace quantities of acid in the hydrocarbon stream produced by a sulfuric acid alkylation process interferes with the above-described downstream processing by causing corrosion and fouling in the equipment used. Consequently, it is an essential feature of the downstream processing of a sulfuric acid catalyzed alkylate to treat the hydrocarbon stream exiting the hydrocarbon-acid separator of an alkylation unit with caustic so as to remove the traces of acid catalyst present. For treating alkylate where no anionic surface active agent was used and no surface active agent is contained therein, a caustic scrub using 5-6% wt. sodium hydroxide followed by a water wash is satisfactory. However, when the alkylate is produced in an anionic surface active agent (i.e., dodecylbenzenesulfonic acid) promoted system and contains some of the surface active agent, the surface active agent tends to act as an emulsifier so as to form a hydrocarbon-water emulsion or a bulky interface which is relatively stable and separates very slowly. These tendencies in the downstream processing of alkylate limit the practical usefulness of anionic surface active agents as alkylation promoters.

I have found that the emulsification and bulky-interface formation tendencies of alkylate containing traces of an anionic-type surface active agent can be modified by controlling the concentration of the caustic scrub solution. In may process, emulsification or the formation of a bulky interface do not occur. Instead, the anionic-type surface-active agent separates as a flocculent precipitate at the caustic-hydrocarbon interface in the caustic-hydrocarbon separator. This type of precipitate does not normally cause operational difficulties.

The water-caustic solution and the hydrocarbon stream mixture entering the hydrocarbon-caustic separator may be mixed in any suitable ratio to obtain the desired flocculent precipitate at the hydrocarbon-caustic interface in the hydrocarbon-caustic separator. Preferably, the ratio is approximately between about 4 parts (vol.) to about 45 parts (vol.) hydrocarbon stream to about 1 part (vol.) water-caustic solution. More preferably, the mixing ratio is about 1 part (vol.) water-caustic solution to about 10 parts (vol.) hydrocarbon stream.

Temperatures and pressures are not critical. The temperature is generally ambient and the pressure is any suitable pressure needed to maintain the isobutanerich stream in a liquid phase and to process the hydrocarbon stream containing the water-caustic solution into the hydrocarbon-caustic separator (i.e., 100 to 500 psi or greater). Preferably, the pressure is between 100 psi to about 350 psi. More preferably the pressure is between 150-175 psi.

I have also discovered that the hydrocarbon stream containing the water-caustic solution should be introduced into the hydrocarbon-caustic separator at a position above the hydrocarbon-water-caustic solution interface within the hydrocarbon-caustic separator. Introduction should be such that the hydrocarbon stream containing the water-caustic solution will enter the hydrocarbon-caustic separator and separate by gravity in a quiescent, non-turbulent manner. Conventional refinery caustic wash units utilize a distributor and baffle apparatus to cause turbulence.

In the following is set forth an example of our invention which is given by way of illustration and not limitation. The specific concentrations, compounds, etc. set forth in the example are not to be construed to unduly limit the scope of the invention.

EXAMPLE 1

A laboratory downstream processing unit intended to simulate the hydrocarbon stream processing of a sulfuric acid catalyzed alkylation unit was constructed. A simulated alkylation stream consisting of isooctane containing 0.0125% dodecylbenzensulfonic acid was passed through this unit. When subjected to an initial water wash (0% caustic) a milky-white stable emulsion was formed in the separator. A similar milky-white, stable emulsion was formed when the strength of the caustic-water wash solution was increased to 1% caustic. When the strength of the caustic-water solution was increased to 5%, a large-volume, bulky, grey-colored interface was formed between the hydrocarbon and caustic layers which amounted to 1.5% (vol.) of the hydrocarbon throughput. A fourth run was made with the same hydrocarbon using an initial 15% caustic wash. In this case, a characteristic flocculent-type precipitate occurred at the interface. The filtration characteristics of such a precipitate do not normally present operational difficulties.

If an alkylate produced by an anionic surface active agent promoted sulfuric acid catalyzed process and which contains some of the surface active agent which partitioned therein is treated with a water wash, a milky-white hydrocarbon-water stable emulsion is formed which is relatively stable and separates very slowly so that further processing is impractical. If a dilute caustic (i.e., water-caustic solution having 1% wt. concentration of caustic) solution is used in place of pure water in the wash step, the surface active alkylation promoter in the hydrocarbon stream is converted to the sodium salt which separates as a bulky interface at the interface between the hydrocarbon and caustic layers of the separator. An additional characteristic of this manner of processing is that the interface formed consists primarily of hydrocarbon and caustic solution having a definite structure which floats at the hydrocarbon/caustic interface. The quantity of interface formed is substantially greater than that expected from the surface active alkylation promoter alone. In some cases I have determined the quantity of interface to be approximately 10% by volume of the hydrocarbon throughput and consisted of 70% by volume of hydrocarbon and 30% by volume of caustic solution. I have discovered that if a water-caustic solution having at least 15% by weight caustic is mixed with the hydrocarbon stream (exiting the hydrocarbon-acid separator of an alkylation unit using an anionic surface active agent promoter and catalyzed with sulfuric acid) prior to introduction into the hydrocarbon-caustic separator of the hydrocarbon-water-caustic stream containing the surface active alkylation promoter the characteristics of the interface are different than either with the pure water wash or with the dilute caustic wash. With a concentration of at least 15% wt., the promoter is converted to the sodium salt as with dilute caustic. However, I have discovered that the hydrocarbon/caustic interface in the hydrocarbon-caustic separator is a flocculent precipitate having a different chemical structure and a much smaller quantity than in the case of the dilute caustic. These characteristics make it possible to separate the promoter salt using conventional filtration techniques.

The caustic concentration in the caustic water scrub solution depends on the type of anionic surface active alkylation promoter used. For the preferred dodecylbenzene sulfonic acid promoter, I have found that a caustic concentration of at least 15% wt. is needed to obtain a flocculent precipitate. For other promoters (such as decylbenzenesulfonic acid) it has been discovered that at least 25% wt. concentration of caustic is needed. Generally, the upper limit of the concentration for all anionic type promoters is approximately 50% wt.

While the present invention has been described herein with reference to particular embodiments thereof, and specific examples, a latitude of modifications, various changes and substitutions are intended in the foregoing disclosure, and in some instances some features of the invention will be employed without a corresponding use of other features without departing from the scope of the invention as set forth.

I claim:

1. In a continuous process for treating an alkylate-containing hydrocarbon phase exiting from an anionic surfactant-promoted, sulfuric acid-catalyzed alkylation unit, wherein the hydrocarbon phase contains said alkylate, unreacted isoparaffin, traces of the sulfuric acid alkylation catalyst and doecylbenzenesulfonic acid alkylation promotor, the improvement comprising,
    a. mixing said hydrocarbon stream with a water caustic solution, having at least 15% by wt. concentration of caustic, such that the salt of the promotor appears as a flocculent precipitate at the hydrocarbon-caustic interface in a hydrocarbon-caustic separator, and (b) introducing the hydrocarbon-caustic mixture into a hydrocarbon-caustic solution separator at a position above said hydrocarbon-caustic solution interface within said hydrocarbon-caustic separator, by allowing the hydrocarbon-caustic mixture to fall by gravity from the introduction point into said hydrocarbon-caustic solution separator, and thus allowing separation of the hydrocarbon stream from the hydrocarbon-caustic solution mixture to be accomplished in a quiescent, non-turbulent manner.

2. The process of claim 1 wherein said water-caustic solution and said hydrocarbon phase are respectively mixed in a ratio of approximately 1:4 to 1:45.

3. The process of claim 2 wherein said ratio is about 1:10.

* * * * *